(12) United States Patent
Huisamen et al.

(10) Patent No.: US 10,265,365 B2
(45) Date of Patent: Apr. 23, 2019

(54) METHOD FOR TREATING OR ENHANCING MUSCLE TISSUE

(71) Applicant: Stellenbosch University, Western Cape Province (ZA)

(72) Inventors: Barbara Huisamen, Durbanville (ZA); Cindy George, Durbanville (ZA)

(73) Assignee: Stellenbosch University, Western Cape Province (ZA)

( * ) Notice: Subject to any disclaimer, the term of this patent is extended or adjusted under 35 U.S.C. 154(b) by 47 days.

(21) Appl. No.: 15/126,870

(22) PCT Filed: Mar. 19, 2015

(86) PCT No.: PCT/IB2015/052024
§ 371 (c)(1),
(2) Date: Sep. 16, 2016

(87) PCT Pub. No.: WO2015/140752
PCT Pub. Date: Sep. 24, 2015

(65) Prior Publication Data
US 2017/0087198 A1    Mar. 30, 2017

(30) Foreign Application Priority Data

Mar. 19, 2014    (ZA) .................................. 2014/01988

(51) Int. Cl.
*A61K 36/48*    (2006.01)

(52) U.S. Cl.
CPC .................................. *A61K 36/48* (2013.01)

(58) Field of Classification Search
None
See application file for complete search history.

(56) References Cited

U.S. PATENT DOCUMENTS

2005/0238736 A1* 10/2005 Mitra ................... A61K 9/0095
424/725

OTHER PUBLICATIONS

George et al. (2011) Journal of Ethnopharmacology, 137: 298-304. (Year: 2011).*
George et al. (2015) Nutrients, 7, 815-830. (Year: 2015).*
George et al. (2015) British Journal of Applied Science & Technology, 10(4): 1-10. (Year: 2015).*
George, C. et al., "The efficacy of Prosopis glandulosa as antidiabetic treatment in rat models of diabetes and insulin esistance", Journal of Ethnopharmacology. 2011, vol. 137, pp. 298-304 abstract, p. 299 para 4, p. 299 para 9, p. 304 para 1-2.
George, C., "Effects of Prosopis Glandulosa on Skeletal Muscle Fatigueability of Rat Soleus Muscle in Adult Wistar Rats", 57th Annual Academic Day Stellenbosch University Faculty of Medicine and Health Sciences, Aug. 14-15, 2013, p. 70 X whole document.
Huisamen, B. et al., "Cardioprotective and anti-hypertensive effects of Prosopis glandulosa in rat models of pre-diabetes", Cardiovascular Journal of Africa. 2013, vol. 24, No. 2, pp. 10-16 abstract, p. 11 para 3-5, p. 16-para 3-4.
Kumar, R. S. et al., "Antitumor Activity of Prosopis glandulosa Torr. on Ehrlich Ascites Carcinoma (EAC) Tumor Bearing Mice", Iranian Journal of Pharmaceutical Research. 2011, vol. 10 , pp. 505-510 abstract, p. 506 para 3-6, p. 509 para 4.
Rahman, A. A. et al., "Antiparasitic and Antimicrobial Indolizidines from the Leaves of *Prosopis glandulosa* var. *glandulosa*", Planta Medica. 2011, vol. 77, pp. 1639-1643 whole document.

* cited by examiner

*Primary Examiner* — Christopher R Tate
*Assistant Examiner* — Russell G Fiebig
(74) *Attorney, Agent, or Firm* — Cesari & McKenna, LLP

(57) ABSTRACT

The use of plant material from the *Prosopis glandulosa* tree (commonly known as Honey mesquite) is described for aiding sporting ability, and in particular for preventing and/or treating muscle injury and enhancing muscle strength. The plant material is typically the dried and ground pods from the tree, but could also be from other parts of the tree, such as the leaves, bark or roots.

13 Claims, 8 Drawing Sheets

METHOD FOR TREATING OR ENHANCING MUSCLE TISSUE

CROSS REFERENCE TO RELATED APPLICATIONS

This application is the National Stage of International Application No. PCT/IB2015/052024, filed on Mar. 19, 2015, which claims the benefit of South African Application No. 2014/01988, filed on Mar. 19, 2014. The contents of both applications are hereby incorporated by reference in their entirety.

FIELD OF THE INVENTION

The invention relates to the use of *Prosopis glandulosa* for treating and enhancing muscle tissue.

BACKGROUND TO THE INVENTION

From accumulating scientific evidence, it is apparent that the phyto-chemicals present in herbal substances have beneficial effects on long-term human health and can be used to effectively treat various diseases.

Numerous studies have shown that antioxidants, such as found in herbal preparations, can result in prolonged performance in endurance exercise, by decreasing oxidative stress [Zheng et al., 2012; Chen et al., 2011; Bucci, 2000] as well as aiding in the muscle regenerative process, resulting in accelerated muscle recovery following muscle injury. Korean ginseng is one example of a herbal preparation shown to enhance exercise and sport performance [Chen et al., 2011; Bucci, 2000; Wang et al., 2010], and a grape-seed derived polyphenol, for example, has recently been described as providing accelerated skeletal muscle recovery [Myburgh et al., 2012; Kruger et al., 2014].

However, the abilities of many herbal remedies to enhance exercise and sport performance or reduce inflammation, as a result of injury, are based on anecdotal claims and lack scientific evidence. Therefore, as a result, many people experience unpleasant or undesirable side effects, due to incorrect dosage and interaction with other prescription medication, when taking commercially available herbal supplements which are unresearched. In addition, synthetic pharmaceuticals are also known for enhancing sport performance or recovery. However many of these (such as non-steroidal anti-inflammatory drugs) are not permitted in competitive sports.

SUMMARY OF THE INVENTION

Figure 1:
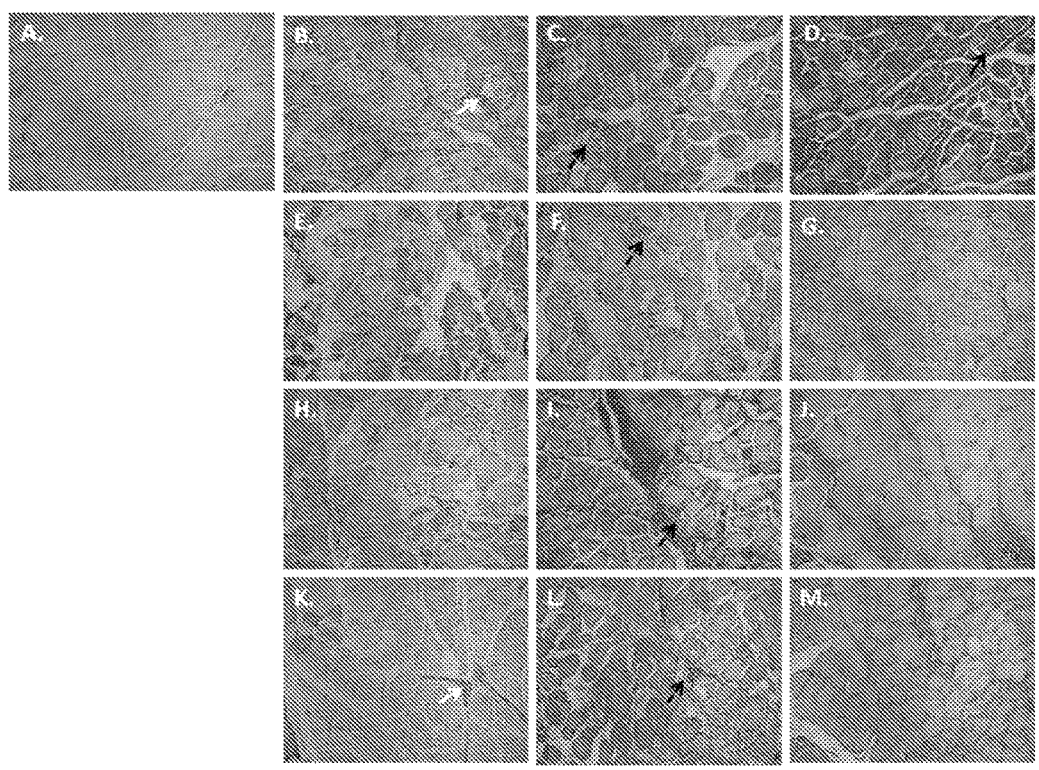
FIG. 1 shows ultrastructural changes over time after experimental contusion injury, stained by H & E. Figure (A) represent uninjured samples; FIGS. (B-D) represent samples taken from PLA animals at 3 h (B), 1 day (C) and 7 days (D) post-injury; Figures (E-G), (H-J) and (K-M) represent similar time points in the PG-CHR, PG-Al and NSAID groups respectively. Scale bar represents 100 µm; Figures (B), (E), (H) and (K) represent muscle fiber destruction and vascular disruption; Immune cells infiltration into the injured area is visible from 1 day post-injury (Figures (C), (F), (I) and (L)). Solid white arrows indicate red blood cells, solid black arrows points to newly regenerated muscle fibers and dashed arrows indicate immune cells.

According to a first embodiment of the invention, there is provided a composition for treating or enhancing muscle tissue in a subject, the composition comprising plant material from *Prosopis glandulosa* or an extract thereof.

The plant material could be from any part of the *P. glandulosa* plant, such as leaves, flowers, roots, stems, bark, seeds and the like. Preferably, the plant material is from seed pods of *P. glandulosa*, and even more preferably, the plant material is from seed pods which have been dried and ground.

The composition may further include pharmaceutically acceptable excipients, binders, adjuvants or fillers.

The composition may be in an oral formulation, such as in the form of a tablet, sublingual tablet, wafer, sachet, capsule, suspension, syrup, powder, liquid beverage or edible bar. Alternatively, the composition may be in a topical formulation, such as a suspension, gel, cream or ointment which may be applied to the skin in the region of the muscle tissue. The composition may also be in an injectable formulation. The composition may also be in the form of a nutritional or dietary supplement.

The muscle tissue to be treated or enhanced is preferably skeletal muscle.

In one embodiment, the composition according is for preventing, minimising or treating muscle injury, such as a direct impact injury. The direct impact injury may be a contusion injury.

In an additional or alternative embodiment, the composition may be for enhancing muscle strength.

The subject may be a human.

The composition may be intended to be administered to the subject at a daily dosage of *P. glandulosa* of from about 50 to about 200 mg/kg/day, such as about 100 mg/kg/day.

According to a second embodiment of the invention, there is provided the use of *P. glandulosa* or a part or extract thereof in a method of making a medicament for treating or enhancing muscle tissue in a subject.

The medicament may be a composition substantially as described above.

According to a third embodiment of the invention, there is provided a method for treating or enhancing muscle tissue in a subject, the method comprising the step of administering plant material from *Prosopis glandulosa* or an extract thereof to the subject.

According to a fourth embodiment of the invention, there is provided a method for preventing, treating or minimising muscle injury in a subject, the method comprising the step of administering plant material from *Prosopis glandulosa* or an extract thereof to the subject.

According to a fifth embodiment of the invention, there is provided a method for increasing muscle strength in a subject, the method comprising the step of administering plant material from *Prosopis glandulosa* or an extract thereof to the subject.

DETAILED DESCRIPTION OF THE INVENTION

The use of plant material from the *Prosopis glandulosa* (Torr.) [Fabaceae] tree (commonly known as Honey mesquite) is described herein. The plant material is typically the dried and ground pods from the tree, but could also be from other parts of the tree, such as the leaves, bark or roots.

Due to their high protein content, the pods of *P. glandulosa* have traditionally been used as a food or general food supplement by the residents of the south-western regions of the North American deserts [Simpson, 1977; Zimmermann, 1991]. This plant species was commonly found in the dry, arid regions of the northern and north-western Cape, South Africa [Jurriaanse, 1973; Harding, 1987], but due to its invasive potential is now classified as a category 2 invader under the Conservation of Agricultural Resources Act of 1983 (Act No. 43 of 1983) [Zimmermann, 1991].

Very few studies have been conducted on the *P. glandulosa* plant and the only literature which could be found regarding its potential clinical benefits were from the Applicant's own studies relating to diabetes and cardiovascular health [26,27, George et al., 2011; Huisamen et al., 2012]. The Applicant is not aware of any literature on the effect of *P. glandulosa* on force generation, fatigue tolerance or muscle recovery after injury.

The Applicant has now found that administration of *P. glandulosa* results in an increase in muscle strength and is also effective in pre- and/or post-injury treatment of muscle injury and inflammation. Material from *P. glandulosa* could therefore be useful for aiding sporting ability, in a dietary or nutritional supplement for enhancing muscle function or performance, as a preventative chronic supplement for preventing or minimising muscle injury or as an acute therapeutic application for treating or speeding up recovery after an injury.

Soft tissue injuries are very common, accounting for between 35% and 55% of all sporting injuries [1]. Soft tissue injuries can result in significant pain, swelling and bruising, culminating in delayed and impaired functionality of the affected muscle [2]. The pathophysiology of muscle injuries is a complex process, progressing through a sequence of overlapping phases, which include degeneration, inflammation, regeneration and the formation of fibrotic scar tissue [3,4,5,6]. Injuries to skeletal muscle not only damage the muscle cells, but may also lead to capillary rupture, infiltrative bleeding, inflammation, oxidative stress and fibrosis, depending on the extent of the injury. Inflammation stands central to these processes, with inflammatory cytokines largely responsible for modulating the cellular environment, thereby largely controlling the progress of other repair processes.

In recent years, researchers have focused on manipulation of inflammation to accelerate muscle regeneration, for example, by targeting immune cells activated during the inflammatory phase [7,8]. Neutrophils and macrophages enter the site of injury in response to chemotactic signals and phagocytize the local debris [5,9,10]. Neutrophils, along with macrophages and satellite cells, release oxygen free radicals, resulting in oxidative stress and direct damage to surrounding tissue unaffected by the primary injury, which results in secondary muscle damage. However, even though early stage phenotypes of macrophages partially contributes to the sustainability of the inflammatory response and thus also secondary damage, these cells also secrete various growth factors that directly contribute to tissue repair and regeneration [5,11]. Additionally, both neutrophils and macrophages stimulate the release of cytokines (IL-1, IL-6, IL-8) and other chemotactic factors by T-cells, which inevitably results in the recruitment of satellite cells, with thus a greater capacity for muscle regeneration [5,12,13]. It is therefore clear that the inflammatory response, even though a contributor to secondary damage, is crucial to the repair of skeletal muscle after injury. Thus in the event of this total process being severely blunted for a prolonged period of time, such as through non-steroidal anti-inflammatory drug (NSAID) treatment, the potential clinical outcome may be suboptimal, resulting in delayed and/or incomplete tissue healing, as well as excessive scar formation, which increases the risk for recurrence of injury. There is evidence that suggests that the prolonged inhibition of the cyclooxygenase-2 pathway (more than 7 days continually) with prostaglandin inhibitors (NSAIDs) compromises muscle repair [4,14,15]. In addition to the use of NSAID's, there are various other muscle injury treatment options, such as the RICE approach (rest, ice, compression and elevation) [4,16, 17,18], therapeutic ultrasound [19,20], hyperbaric oxygen therapy [21] and the use of growth factors [22]. However, these therapies remain suboptimal, as in many instances it either does not translate into increased myotube formation, therefore does not enhance muscle healing [19,20] and may be associated with severe risks and side effects [23].

Physical fatigue, also referred to as peripheral fatigue, is denoted as the deterioration of muscle performance during prolonged activity [Roots et al., 2008; Fitts, 1994]. This decrease in force is reversible, as muscle performance can be recovered after sufficient rest and appropriate nutrition.

The magnitude of muscle force generation is determined by two main factors, namely, (i) the size of the muscle recruited to generate the force and (ii) the muscle fiber type [Maughan et al., 1983; Lee et al., 2013]. Force generation during contraction is related to the number of cross-links made between the actin and myosin chains [Fitts et al., 1991]. Therefore, the more cross-links formed, the stronger the force of contraction. Hence, the maximal force of contraction depends upon the number of fibers a muscle contains. The type of fibers also plays an important role, as different types of muscle fibers possess different contractile properties [Schaiffino and Reggiani, 2011]. It is known that a muscle composed of a high proportion of slow-twitch (Type I) fibers will be relatively weaker than a muscle of similar size with a high proportion of fast-twitch (Type II) fibers. Fiber composition is regulated in response to changes in physical activity, environment and pathological conditions [Schiaffino et al., 2007], for example, endurance exercise training induces a fast-to-slow fiber type transition, transforming the myofibers to an increased oxidative metabolism [Demirel et al., 1999; Pette and Staron, 2001; Yuan et al., 2011]. Additional factors leading to fiber type transition include mechanical loading and unloading, hormones and aging [Pette and Staron, 2001].

The data from this study indicates that *P. glandulosa* treatment might prove beneficial as a supplement, aiding physical ability, and results in more effective muscle repair after contusion injury than without treatment or with NSAID treatment.

The fact that *P. glandulosa* is categorized as an invader tree in South Africa, and possibly in other countries too, illustrates the ethnopharmacological significance of these findings. The use of an economical, natural and readily available substance as treatment, could have far-reaching implications in not only the sporting arena and health sector, but also in plant and wildlife conservation.

The invention will now be described in more detail by way of the following non-limiting examples.

Example 1: Preventative and Therapeutic Application of *P. glandulosa* for Soft Tissue Injuries

*P. glandulosa* as a possible pre- and/or post-injury treatment option after a contusion injury was studied. Effects on neutrophil and macrophage infiltration into the injured area were investigated, as well as associated consequences in the context of muscle regeneration. A recognized NSAID commonly used in the treatment of muscle injury and inflammation (diclofenac) was used as a comparative control.

Materials and Methods

Animals

Age- and weight-matched adult, male, Wistar rats were divided into four main groups, namely: (1) control placebo (PLA); (2) PG-CHR, animals treated with *P. glandulos* for 8 weeks prior to injury and after injury, up to the time of sacrifice; (3) PG-Al, animals treated with *P. glandulosa* after injury (first treatment, 2 h after injury), up to the time of sacrifice and (4) NSAID, animals treated with Voltaren Emulgel® (diclofenac) directly after injury, up to the time of sacrifice. All four groups were subdivided into sacrifice and data collection time points of t=0 h (before injury), 1 h, 3 h, 1 day and 7 days, post-injury. Each main group had an n=25, i.e., 5 rats per time point per group (total of 100 rats).

Rats in the different experimental groups were matched for body mass at the start of the protocol (PLA: 456.47±9.74 g; PG-CHR: 445.98±11.21 g; PG-Al: 439.12±14.84 g; NSAID: 442.25±12.58 g).

*P. glandulosa* and Diclofenac Treatments

*P. glandulosa* powder consisting solely of dry-milled *P. glandulosa* pods was used in this experiment [26]. To prepare treatment, *P. glandulosa* powder from *P. Schoeman* was weighed daily for each animal in the treatment group and set into a mixture of commercially available gelatine/ jelly cubes of 1 mL volume. These jelly cubes were fed to each animal individually for 8 weeks, to ensure absolute compliance and dose control. The dosage of 100 mg/kg/day *P. glandulosa* was calculated based on the daily dosage prescribed for human adults on a commercially available food supplement. This dose has previously been shown by the Applicant to elicit beneficial metabolic changes in rats [26,27]. During the 8-week experimental period, the control animals received placebo jelly cubes.

Diclofenac, a known NSAID, served as a positive control for the anti-inflammatory effects of treatment. Diclofenac sodium, in the form of Voltaren Emulgel® from Novartis, was applied topically to the injured area on the hindlimb of the rats after different time periods post-injury. The dosage of Voltaren Emulgel® was calculated at 57.14 mg/kg/day, which was equal to 0.57 mg/kg Diclofenac. The dosage was calculated based on the daily dosage prescribed for human adults.

Induction of Experimental Muscle Contusion Injury and Sample Collection

The contusion injury to the rat hind-limb was produced using the mass-drop model injury first described by Stratton et al. (1984) [28] and optimized for our laboratory by Myburgh and colleagues (2012) [7]. Briefly, the technique entails dropping a 200 g weight from the height of 50 cm onto the medial surface of the right gastrocnemius muscle of sodium pentobarbital (40 mg/kg, intraperitoneal) anaesthetized rats. This contusion injury was moderately severe, did not result in bone injury or affect gait in the injured animals.

For sample collection, rats were euthanized by sodium pentobarbital overdose (200 mg/kg, intraperitoneal) and the central section of the damaged gastrocnemius muscle harvested. The harvested muscle was divided into two parts, one part processed for immunohistochemistry and the other part snap-frozen for Western blotting analysis.

Muscle Histology and Immunohistochemistry

For cross-sectional histology and immunohistochemistry, muscles were fixed in 10% formal saline, processed and embedded in paraffin wax. Five-micrometer thick cross-sections were prepared (Leica RM 2125 RT microtome, Nussloch, Germany) and stained with haematoxylin and eosin (H & E) for qualitative histological analysis.

Immunostaining with mouse anti-rat His48 (neutrophil; 1:200; Santa Cruz Biotechnology, Santa Cruz, Calif., USA), goat anti-mouse F4/80 (macrophage; 1:200; Santa Cruz Biotechnology, Santa Cruz, Calif., USA) and rabbit anti-human desmin (1:200; Santa Cruz Biotechnology, Santa Cruz, Calif., USA) antibodies was performed on the fully automated Leica Bond-Max Autostainer system (Leica Microsystems, Germany) using an onboard detection kit, which included the Bond Epitope Retrieval Solution, peroxide block, primary antibody, post primary reagent, Bond Wash solution and Bond Polymer [29,30]. DAB (3,3'-diaminobenzidine tetrahydrochloride) was used as the chromogen (Leica Microsystems, Germany). Appropriate positive controls were used throughout the study.

Image Analysis

All imaging data were obtained by analyzing two sections from each muscle sample, at each time point for each antibody. In the injured area, five fields of view per section were imaged using a microscope (Nikon ECLIPSE E400; 400× objective used), equipped with a color digital camera (Nikon 5.0 Mega Pixels Color Digital Camera head DS-Fi2). The images presented in this article are only partial images of those taken at 200× magnification. Photos were used to count positively labeled neutrophils, macrophages and desmin-stains. Immune cells were counted manually and expressed as the average number of positively labeled immune cells per field of view (350 μm$^2$) in the injured area, using the NIS-Elements BR imaging software package. In order for a cell to be classified a true neutrophil and macrophage, it had to have multilobular nuclei or single nuclei with surrounding cytoplasm, respectively.

Western Blotting

Protein levels were determined by standard Western blotting technique [26]. Briefly, proteins were extracted from the gastrocnemius muscle tissue, equal concentration of total protein loaded and separated on a SDS poly-acrylamide gel and electro-transferred to Immobilon™-P PVDF membranes. Ponceau red reversible stain was used to determine transfer efficacy of proteins. The membranes were incubated overnight in ADAM$_{12}$ primary antibody (1:5000; Abcam, England, UK). For detection, horseradish peroxidase coupled secondary antibody (1:4000; Amersham Life Sciences, Sandton, J H B, South Africa) was used. Antigen-antibody complexes were visualized using ECL detection reagent (Amersham Life Sciences, Sandton, JHB, South Africa) and exposed to an autoradiography film (Hyperfilm ECL, RPN 2103) and light emission was detected. All films were analyzed by means of densitometry (UN-SCAN-IT; Silk Scientific Inc., Utah, Utah, USA) and normalized data expressed in arbitrary units (AU). In all instances the membranes were stripped, by incubating in 0.2 M NaOH and reblotted with antibody against β-tubulin (1:1000; Cell Signalling Technology, Beverley, Mass., USA) to verify the uniformity of protein load across the test samples.

Statistical Analysis

All data are presented as mean±standard error of the mean (SEM). Statistical significance was analyzed by a two-way ANOVA, followed by a Bonferroni post hoc test. $p<0.05$ was considered as statistically significant. Statistical analysis of data was performed using GraphPad Prism version 5.

Results

Chronic *P. glandulosa* Treatment Accelerates Repair of Muscle Ultrastructure

Qualitative microscopic analysis of the fiber architecture post-contusion injury indicated that irrespective of treatment, the blunt force to the muscle belly significantly damaged and disrupted the skeletal muscle fibers, resulting in red blood cell accumulation in the interstitial spaces at 1 h and 3 h after injury (FIG. 1B,E,H,K). Representative pictures for 1 h after injury are not included as differences between 1 and 3 h post-injury cannot be easily discerned visually. Edema was present in both treated and untreated groups, confirmed by the widening of the interstitial spaces between the fibers at this early time point. Histological comparison between the placebo (PLA) and the treatment groups illustrated a significant influx of immune cells 1 day after injury in all four groups. However, this influx was relatively limited in the group chronically treated with *P. glandulosa* (PG-CHR), when compared to all other groups. The immune cells remained visible in the injured area of the PLA, post-injury treated group (PG-AI) and the non-steroidal anti-inflammatory treated (NSAID) groups for up to day 7 post-injury (FIG. 1D,J,M), but were undetectable in the PG-CHR group at the same time point (FIG. 1G). By day 7 only the chronically treated *P. glandulosa* group (FIG. 1G) displayed near normal muscle architecture, indicative of successful progressing muscle regeneration.

*P. glandulosa* Treatment Blunted the Neutrophil Response to Contusion Injury

Figure 2:
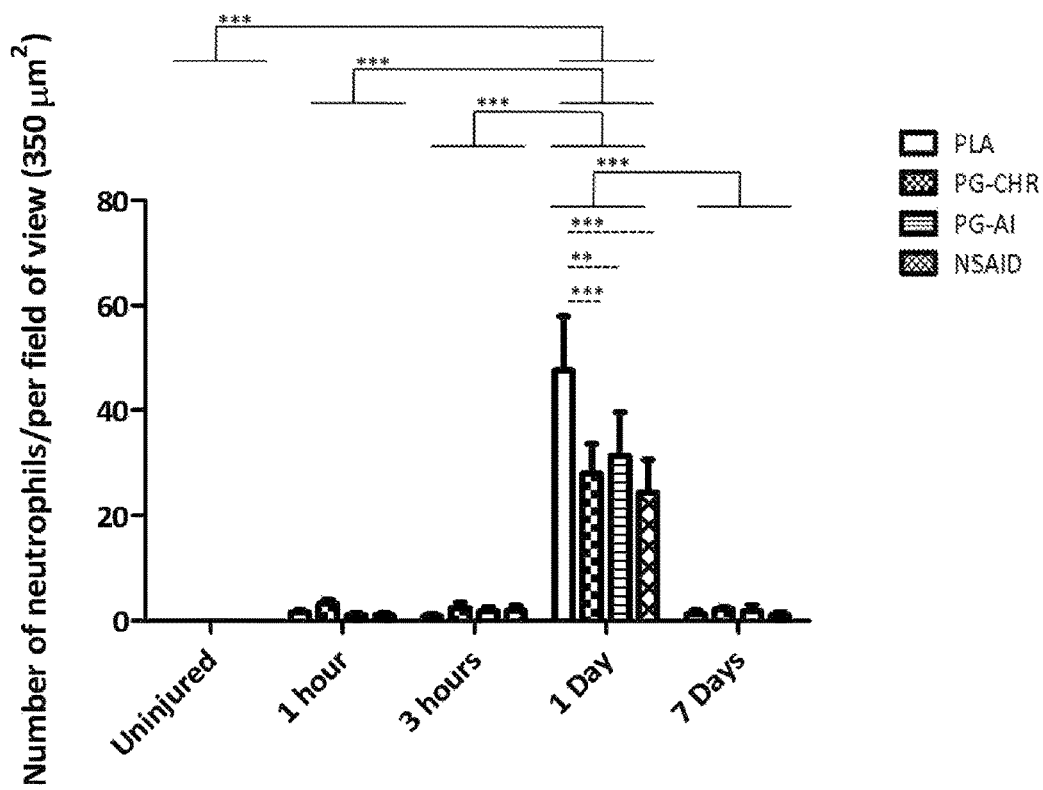
FIG. 2 shows neutrophil (His48 stain) infiltration into injured area after contusion injury with/without *P. glandulosa* treatment. The data are expressed as mean±SEM. Analysis was done by two-way ANOVA. n=5 per time-point/per group; Differences over time are indicated by solid lines and broken black lines indicate group differences at specific time points; Significance: All groups: * $p<0.0001$ uninjured vs. 1 day; 1 h vs. 1 day; 3 h vs. 1 day; 1 day vs. 7 days. 1 Day: * $p<0.0001$ PLA vs. PG-CHR; PLA vs. NSAID; ** $p<0.05$ PLA vs. PG-Al.

Clear differences were evident between the various experimental groups with regards to neutrophil infiltration. No neutrophils were present in the any of the experimental groups before injury, whereas contusion injury resulted in a significant (between 30- and 40-fold) transient elevation in neutrophils on day 1 after injury, which normalised by day 7 post-injury ($p<0.0001$) (FIG. 2). On day 1 post-injury, the PG-CHR ($p<0.0001$), PG-AI ($p<0.001$) as well as the NSAID treatment groups ($p<0.0001$) displayed a significantly lower number of neutrophils compared to the untreated group (PLA). Furthermore, the magnitude of the neutrophil response as assessed on day 1 post-injury was similar in these three treatments groups.

Figure 3:
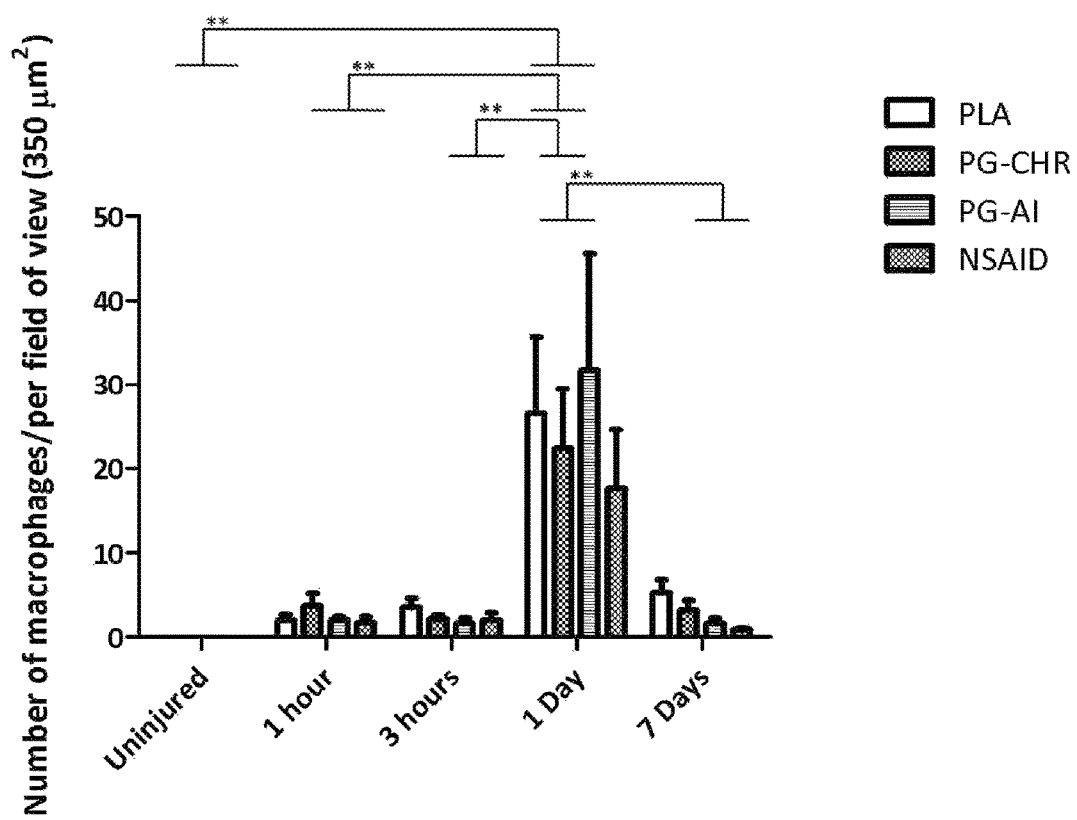
FIG. 3 shows macrophage infiltration into injured area after contusion injury with/without *P. glandulosa* treatment. The data are expressed as mean±SEM. Analysis was done by two-way ANOVA. n=5 per time-point/per group; Differences over time are indicated by solid lines; Significance: All groups: **$p<0.001$ uninjured vs. 1 day; 1 h vs. 1 day; 3 h vs. 1 day; 7 days vs. 1 day.

*P. glandulosa* Treatment Did not Affect Macrophage Response to Contusion Injury Similar to the neutrophil data, the presence of macrophages was undetectable in the uninjured control samples (FIG. 3). Of the time-points assessed, the peak number of macrophages ($p<0.001$) present in the injured area, was 1 day after injury in all four experimental groups. These increased values had again normalised by day 7 after injury ($p<0.001$). None of the treatments seem to have any effect on macrophage infiltration at the time points assessed.

Figure 4:
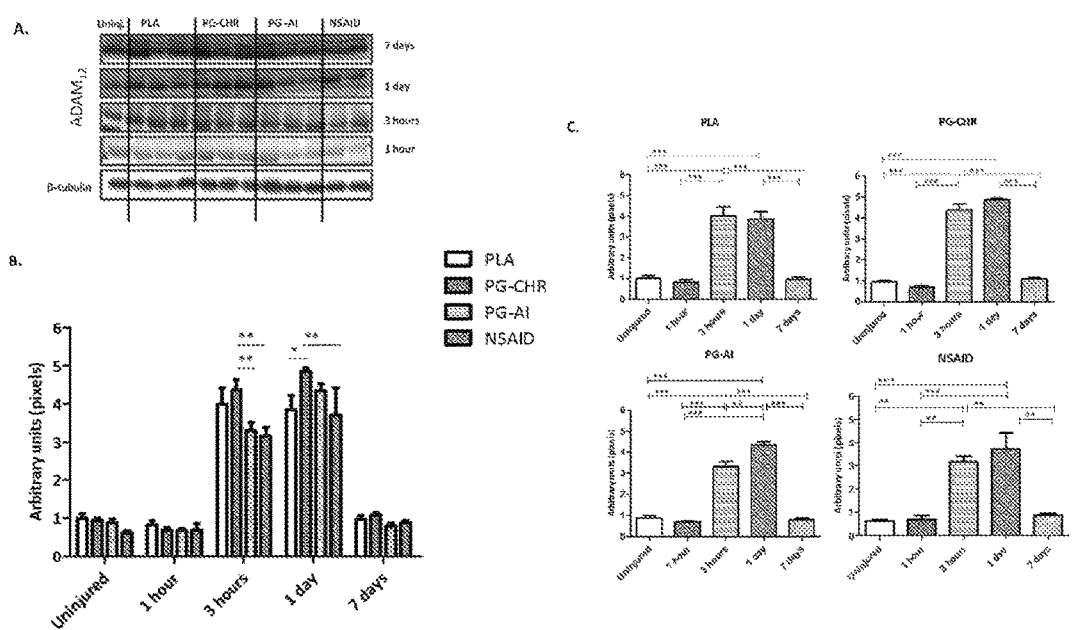
FIG. 4 shows $ADAM_{12}$ expression in skeletal muscle following a contusion injury. (A) Representative Western blots. Top 4 bands represent $ADAM_{12}$ expression and the bottom bands represent β-tubulin expression (confirm equal loading of the protein); (B) Combined data for all the different groups; (C) Statistical differences observed between the different time-points in each experimental group. Values are expressed relative to the uninjured values. The data are expressed as mean±SEM; Analysis by two-way ANOVA; n=5 per time-point/per group; Differences over time are indicated by solid lines and broken black lines indicate group differences at specific time points; Significance: * $p<0.0001$,  $p<0.001$ and * $p<0.05$.

ADAM$_{12}$ Expression is Enhanced in Response to Chronic *P. glandulosa* Treatment According to the Western blot analysis, expression of the satellite cell proliferation marker, ADAM$_{12}$, was significantly elevated from 3 h post-injury ($p<0.0001$) and this significant elevation persisted for at least 24 h ($p<0.0001$), with the expression again normalized to uninjured levels on day 7 after injury, in all experimental groups ($p<0.0001$) (FIG. 4A,B). Of all three treatments assessed, the 8-week chronic treatment with *P. glandulosa* (PG-CHR) showed the most significant effect with significantly increased ($p<0.05$) expression of ADAM$_{12}$, on day 1 post-injury, when compared to the PLA group. Although post-injury treatment (PG-AI) seemed to suppress ADAM$_{12}$ expression at 3 h, when compared to PLA, it was associated with a significant increase in ADAM$_{12}$ expression from 3 to 1 day. NSAID treatment was associated with a similarly suppressed ADAM$_{12}$ expression at 3 h, but with this treatment, the relative suppression persisted at 1 day after injury. Indeed, the NSAID group expressed lower levels of $ADAM_{12}$ compared to the chronically treated *P. glandulosa* group at both 3 h and 1 day post-injury, significantly so on the latter (p<0.001). For the sake of clarity, the statistical differences observed between the different time-points in each experimental group is illustrated in FIG. 4C.

Desmin Expression is Increased in Response to Chronic *P. glandulosa* Treatment

Figure 5:
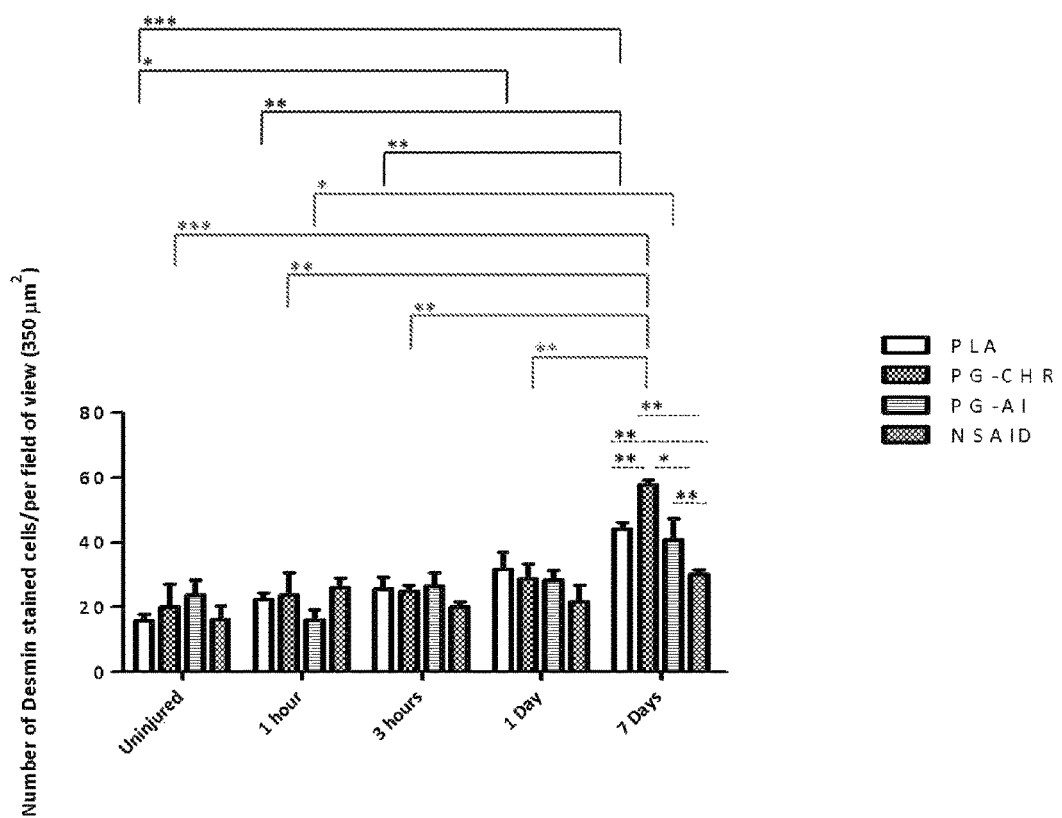
FIG. 5 shows desmin expression in skeletal muscle following a contusion injury. The data are expressed as mean±SEM; Analysis by two-way ANOVA; n=5 per time-point/per group; Differences over time are indicated by solid black lines (PLA), solid blue lines (PG-CHR), solid red lines (PG-Al) and broken black lines indicate group differences at specific time points; Significance: * $p<0.0001$,  $p<0.001$ and * $p<0.05$.

Desmin expression was found to steadily increase after injury, with highest values at the 7 days post-injury time point, in all four different experimental groups. At the 7-day post-injury time-point, the chronically treated *P. glandulosa* group (PG-CHR) displayed significantly elevated desmin expression compared to all other groups (FIG. 5). While post-injury *P. glandulosa*-treatment had no effect on the expression of desmin, the NSAID-treated group displayed significantly decreased desmin expression, when compared to all other groups, indicative of delayed regeneration.

DISCUSSION

Chronic *P. glandulosa* treatment was found to significantly reduce neutrophil infiltration into the injured area, suggestive of a decreased pro-inflammatory signal and probably less neutrophil-associated secondary damage. In support of this interpretation, an associated significant increase in the expression of $ADAM_{12}$ (day 1 post-injury) and desmin (day 7 post-injury) was observed, suggesting an enhanced regenerative process.

Large differences between *P. glandulosa* treatment and the NSAID treatment were evident.

The level of $ADAM_{12}$ expression in gastrocnemius muscles, at different time-points after injury, has not been previously measured in an in vivo model. The fact that chronic *P. glandulosa* treatment increased the $ADAM_{12}$ expression at early time-points relative to the PLA indicates that the treatment may facilitate more effective recovery by enhancing early proliferation. In stark contrast, the NSAID treatment resulted in significantly suppressed $ADAM_{12}$ expression (particularly at 3 h), pointing to an inhibitory effect on repair. This undesired effect was also evident from the desmin response.

Desmin levels usually increase significantly during myogenesis and remain elevated in newly matured myofibers [49], which explains the relative late response in our protocol time course. On day 7, and in accordance with the other data suggesting more effective muscle fiber repair, desmin expression was significantly higher after chronic *P. glandulosa* treatment. In contrast, desmin expression was significantly lower than PLA after NSAID treatment, again pointing to an inhibitory effect of NSAID on repair, as suggested in the literature [3]

Example 2: Effect of *P. glandulosa* on Muscle Strength

The effects of *P. glandulosa* were studied by electrically stimulating the isolated soleus muscle from rats to fatigue and the extent of recovery was determined after the fatigue period as well as the magnitude of force development with and without *P. glandulosa* treatment.

Materials and Methods

Chemicals

All chemicals used were purchased from Merck (Pty) Ltd, South Africa. The *P. glandulosa* preparation was as described in Example 1.

*Prosopis glandulosa* Treatment Regime

Rats were treated with *P. glandulosa* powder at a dose of 100 mg/kg/day for a total period of 10 weeks. *P. glandulosa* was weighed daily for each animal in the treatment group and set in a mixture of commercially available gelatine/jelly cubes of 1 ml volume. These jelly cubes were fed to each animal individually, to ensure absolute compliance and dose control. The dosage of 100 mg/kg/day *P. glandulosa* was calculated based on the daily dosage prescribed for human adults, which has previously been shown by the Applicant to elicit metabolic changes [George et al., 2011; Huisamen et al., 2012]. To accustom the animals to the researcher and the taste of the jelly cubes, all animals were fed placebo jelly cubes (jelly cubes without *P. glandulosa*) for 1 week prior to the start of the actual treatment program. During the 8 weeks experimental period, the control animals received placebo jelly cubes.

Division into Groups

Age and weight matched male Wistar rats were divided into 2 groups: a control placebo group (PLA), that received normal rat chow pellets and jelly cubes without *P. glandulosa* and a *P. glandulosa* group (PG) that received normal rat chow and *P. glandulosa* mixed into jelly cubes (n=10 in each group). A total of 20 isolated muscles were utilized, i.e. 10 animals per experimental group (treatment vs. no treatment).

Sacrifice and Sample Collection

After 10-weeks of *P. glandulosa* treatment, the animals were weighed (to determine body mass) and then received an overdose of sodium pentobarbital (200 mg/kg, intraperitoneal). The animals were continually monitored until loss of consciousness was reached, indicated by a total lack of response after a foot pinch.

Muscle Fatigue Stimulation Protocol

Skeletal muscle fatigue was determined by methods previously described by Gordon et al. (2010) and El-Khoury et al. (2012). After the animals were euthanized with an overdose of sodium pentobarbital (200 mg/kg, intraperitoneal), one of the soleus muscles, with tendinous insertions intact, were removed and placed in ice-cold Krebs-Henseleit buffer (KHB). The KHB solution contained in mM: NaCl 119, KCl 4.74, $CaCl_2.2H_2O$ 1.25, $MgSO_4.7H_2O$ 0.6, $KH_2PO_4$ 1.2, $NaHCO_3$ 24.9, $Na_2SO_4$ 0.6 and glucose 10. The intact soleus muscle was then removed from the cold KHB buffer and vertically suspended between a pair of platinum electrodes in a 25 ml water-jacketed organ bath containing KHB solution. The KHB was continuously gassed (95% $O_2$/5% $CO_2$) to maintain the pH at 7.4 and the temperature of the KHB was kept at 25° C. The physiological stability of rat skeletal muscle in vitro is temperature-dependent and stability for muscle strips of 1-2 mm diameter is better at 25° C. compared to the in vivo temperature of 37° C. [Segal et al., 1986]. The base of the muscle was fixed to an immobile hook and the other end tied to an isometric force transducer. The position of the force transducer could be adjusted by a micro-positioner, thus altering preload. The muscles were left to stabilize for 30 minutes before electrical stimulation commenced.

After an equilibration period of 30 min, the optimal length (i.e. muscle length producing maximal isometric twitch force) and supramaximal voltage were determined. These parameters were determined for each muscle by generating single twitch contractions at increasing muscle lengths and voltages, respectively, until no increase in single-twitch force production was observed. The muscle length and voltage that generated the highest single twitch amplitude was then used throughout the entire stimulation protocol. The pulse duration was set to 1 msec for all twitch and tetanic contractions. The stimulation protocol consisted of the generation of a single twitch, force frequency curve to determine $F_{max}$, tetanus, a 2 minute stimulation period to determine fatigue resistance and ended off with two sets of tetanus stimulations at 5 and 20 minutes after fatigue. $F_{max}$ was determined using brief, repeated stimulations at increasing pulse frequencies (1, 5, 10, 20, 30, 40, 50, 60, 70, 80, 90 and 100 Hz for 3 sec allowing a 2 min recovery interval between each stimulus). The greatest force achieved for each animal using this protocol was considered the $F_{max}$. Following a 10 min resting period after $F_{max}$ determination, muscle fatigue rate was determined over a 2 minute period of intermittent contractions, stimulating the muscle for 2 seconds on and 2 seconds off at a frequency of 40 Hz (predetermined to be $F_{max}$). Force was measured at 20 second intervals during fatigue. Twitch amplitude (force), contraction time (time to peak tension) and half-relaxation time (time for peak force to decay by 50%) were determined before (BF) and after (AF) the fatigue protocol. Contraction time (time to peak tension) was defined as the time elapsed from the base to the peak of a single twitch. Half-relaxation time was defined as the time elapsed from the peak of a single twitch to the point of the twitch amplitude returning halfway to baseline. All muscle function data were collected through an AD Instruments Bridge Amp and Powerlab 4/30, and analyzed with Chart5 PowerLab software (ADInstruments, Inc., Colorado Springs, Colo.).

Specific force was calculated in N/cm$^2$ of muscle cross-sectional area. The latter was approximated by dividing the dry-weight of the muscle by the product of optimal length and muscle density (assumed to be 1.056 g/cm$^3$). The force transducer was calibrated using known weights. The contraction time and half-relaxation time were measured as indices of isometric twitch kinetics. For the fatigue protocol, values were normalized by expressing the force generated at each 20 second time point, as a percentage of the initial force at the beginning of the fatigue trial.

Statistical Analysis

All data are presented as mean±standard error of the mean (SEM), unless otherwise stated. Statistical significance between two groups was assessed via a Student t-test and between two or more groups, a two-way ANOVA was used, followed by a Bonferroni post-hoc test. p<0.05 was considered as statistically significant. Statistical analysis of data was performed using GraphPad Prism 5.

Results

Effect of *P. glandulosa* Treatment on Body Mass and Muscle Biometrics

Rats were matched for body mass at the onset of the 10 week *P. glandulosa* treatment and treatment was found to have no effect on weight gain. Skeletal muscle biometrics (mass, optimal length and width), which is a key determinant of the force output, displayed no significant differences between the treated and untreated groups (Table 1). In essence, the soleus muscles of the PLA and PG where biometrically similar.

TABLE 1

Biometric characteristics of the experimental animals after *P. glandulosa* treatment

|  | C-PLA | C-PG | p-values |
|---|---|---|---|
| Body mass (g) | 438.00 ± 14.97 | 426.43 ± 16.26 | Not significant |
| Muscle mass (g) | 0.20 ± 0.01 | 0.19 ± 0.012 | Not significant |
| Muscle dry-mass (g) | 0.03 ± 0.003 | 0.03 ± 0.003 | Not significant |
| Optimal muscle length (mm) | 31.20 ± 0.66 | 31.14 ± 0.99 | Not significant |
| Muscle width (mm) | 4.60 ± 0.24 | 4.43 ± 0.20 | Not significant |
| Muscle mass/ body mass ratio | 0.04 ± 0.002 | 0.05 ± 0.002 | Not significant |

The data are expressed as mean ± SEM; Analysis by Student t-test; n = 10

Contractile Properties of Soleus Muscle

The induction of muscle fatigue resulted in the significant reduction in both twitch- and peak tetanic force generated by the soleus muscle, when comparing PLA (BF) to PLA (AF) and PG (BF) to PG (AF). Therefore, as a consequence, the twitch/tetanus ratio was significantly reduced after fatigue compared to before fatigue. Despite fatigue ensuing, the contraction time was unaffected by *P. glanulosa* treatment, remaining constant throughout. Ten weeks of *P. glandulosa* treatment sufficiently increased force generated by the soleus muscle, as depicted by the significantly elevated twitch- and peak tetanic force production at baseline (PG (AF) vs. PLA (AF)). *P. glandulosa* treatment also resulted in a significantly increased half-relaxation time post-fatigue, compared to the untreated controls (Table 2).

TABLE 2

Contractile properties of soleus muscle from control vs. *P. glandulosa*-treated rats before and after fatigue

|  | PLA (BF) | PG (BF) | PLA (AF) | PG (AF) | p-values |
|---|---|---|---|---|---|
| Twitch force (N/cm$^2$) | 7.80 ± 0.65 | 11.95 ± 0.72* | 3.09 ± 0.41*** | 4.22 ± 0.17*** | *p < 0.05 PG (BF) vs. PLA (BF); ***p < 0.0001 PLA (AF) vs. PLA (BF); PG (AF) vs. PG (BF) |
| Contraction time (ms) | 150.0 ± 10.0 | 114.29 ± 3.49 | 120.00 ± 5.48 | 128.57 ± 5.62 | No significance |
| Half-relaxation time (ms) | 447.5 ± 10.37 | 442.86 ± 11.88 | 387.5 ± 16.01 | 453.21 ± 9.83* | *p < 0.05 PG (AF) vs. PLA (AF) |
| Tetanic force (N/cm$^2$) | 47.91 ± 2.60 | 62.20 ± 2.68* | 26.39 ± 5.98*** | 28.45 ± 1.92** | *p < 0.05 PG (BF) vs. PLA (BF); ***p < 0.0001 PLA (AF) vs. PLA (BF); PG (AF) vs. PG (BF) |
| Twitch/Tetanus ratio | 15.83 ± 1.49 | 19.16 ± 1.50 | 11.90 ± 2.40* | 14.75 ± 1.04* | *p < 0.05 PLA (AF) vs. PLA (BF); PG (AF) vs. PG (BF) |

The data are expressed as mean ± SEM; Analysis by two-way ANOVA; n = 10

Force-Frequency Relationship

Figure 6:
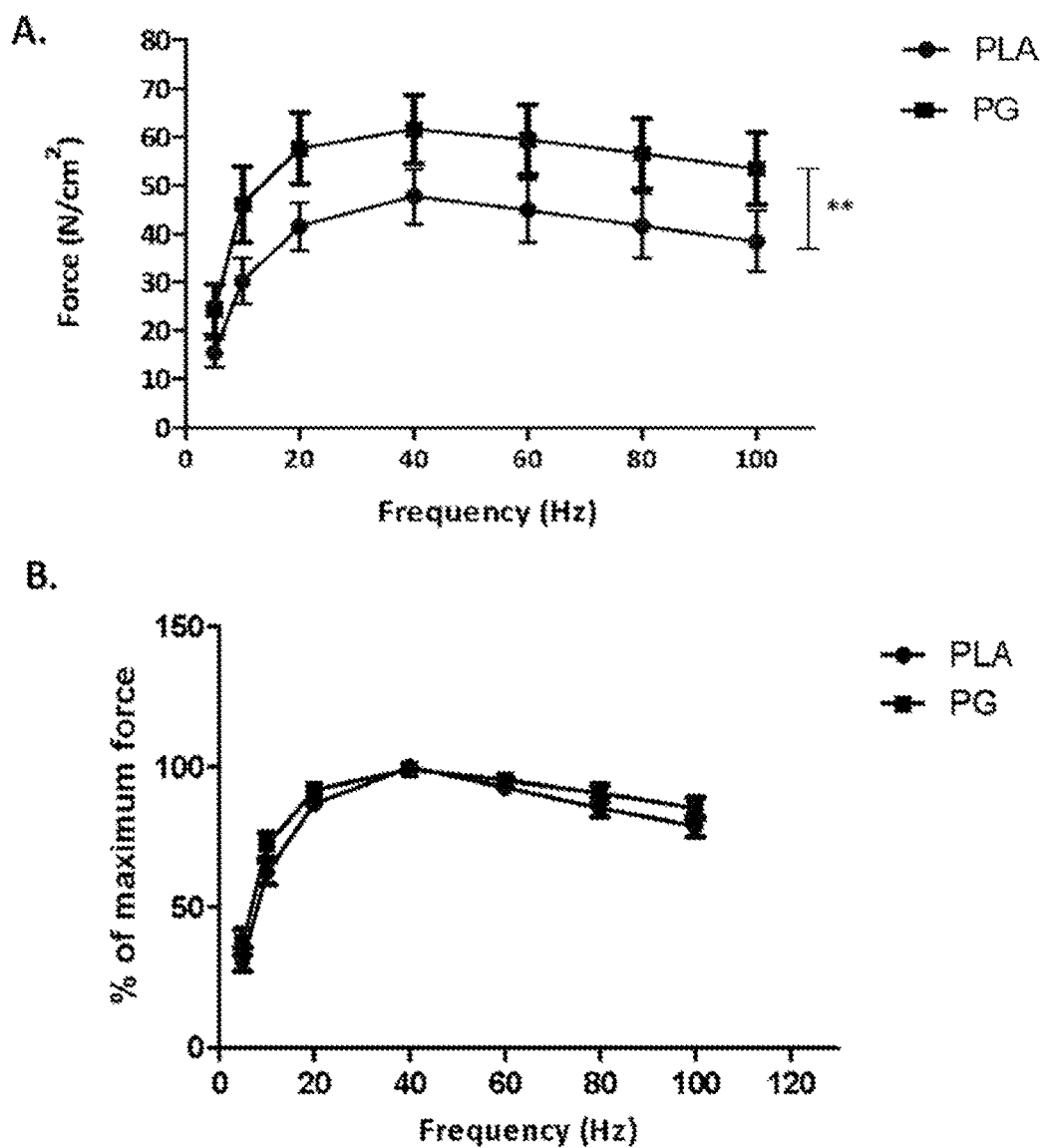
FIG. 6 shows force-frequency relationship characteristics of rat soleus muscle in control and *P. glandulosa*-treated rats. (A) represents the specific force generated by the soleus muscles at the different frequencies and (B) represents the force generated at each frequency when expressed relative to the maximum force generated. Force-frequency curve was generated by means of brief, repeated stimulations at increasing pulse frequencies. The greatest force achieved for each muscle using this protocol was considered the $F_{max}$. The data are expressed as mean±SEM. Analysis were by two-way ANOVA. n=10; ** $p<0.001$ PLA vs. PG (10 Hz to 100 Hz).

The force-frequency relationship, which is the sigmoid relationship between a muscle's activation frequency and the consequent isometric force output, displayed a similar trend for both muscles in the treated and untreated groups. This trend is displayed in FIG. 6 (B), representing the force generated at each frequency, expressed as a % of the maximum force generated. In contrast, the absolute values of the force generated at different frequencies displays that the soleus muscles of the treated rats generated significantly more force, during electrical stimulation, compared to the untreated rats, at all the different frequencies (P<0.001). As illustrated in FIG. 6 (A), the force generated by the soleus muscle of the untreated rats incrementally increased from 15.34±2.92 N/cm$^2$ at a frequency of 5 Hz to a maximum force of 47.77±5.73 N/cm$^2$ at a frequency of 40 Hz, where after the generated force slowly decreased to a force equal to 38.55±6.27 N/cm$^2$ at a frequency of 100 Hz. A similar trend is followed by the treated rats, but at significantly higher levels. The force generated by the soleus muscle of the *P. glandulosa* treated rats incrementally increased from 24.37±3.18 N/cm$^2$ at a frequency of 5 Hz to a maximum force of 61.65±5.05 N/cm$^2$ at a frequency of 40 Hz, before slowly declining to a force of 53.48±6.41 N/cm$^2$ at a frequency of 100 Hz. The level of force generated peaked at a frequency of 40 Hz in both groups.

Fatigue Characteristics

Figure 7:
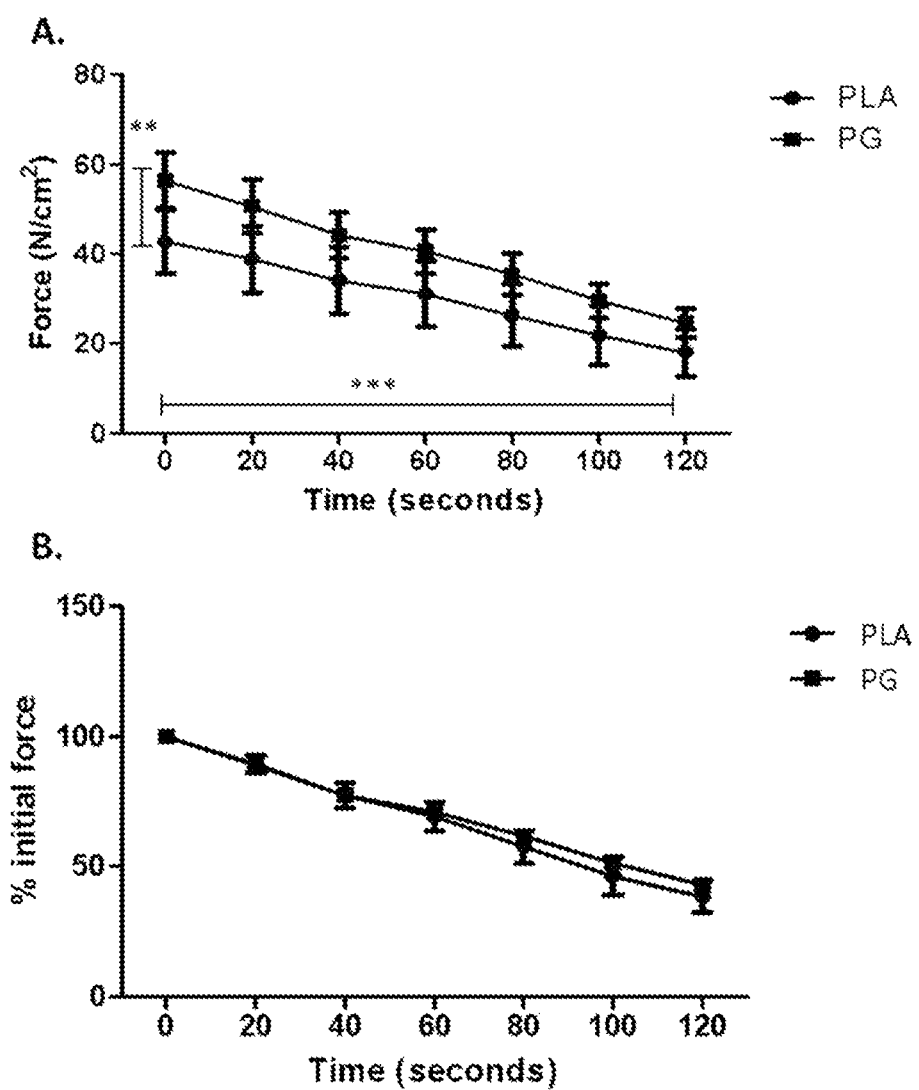
FIG. 7 shows fatigue characteristics for soleus muscle in control and *P. glandulosa*-treated rats. (A) represents the specific force generated by the soleus muscles and (B) represents the force, expressed as a % of the initial force generated. Muscle fatigue was determined over a 2 minute period of intermittent contractions, stimulating the muscle for 2 seconds on and 2 seconds off at a frequency of 40 Hz (predetermined to be $F_{max}$). Force was measured at 20 second intervals during the fatigue protocol. The data are expressed as mean±SEM. Analysis was by two-way ANOVA. n=10;  $p<0.001$ t=0 min; PG vs. PLA; * $p<0.0001$ t=0 min vs. t=120 min PLA; PG.

The 2 minute intermitted stimulation (fatigue protocol) was sufficient to significantly decrease the force generated by both the treated and untreated group by at least 50%. In other words, the force measured after the 2 minute fatigue protocol was 50% lower than the force measured before the induction of fatigue (18.03±3.36 vs. 42.62±5.00 N/cm$^2$; P<0.0001) [FIG. 7 B]. *P. glandulosa* treatment was unable to reduce fatigue tolerance, as fatigue development was not significantly different between the treated versus untreated group at any point during the 2 minute fatigue protocol. However, the initial force generated, was significantly higher in the treated group, when compared to the untreated group (56.39±4.21 vs. 42.62±5.00 N/cm$^2$; P<0.001).

Contractile Properties, Before and after Fatigue

The induction of muscle fatigue resulted in the significant reduction in both twitch- and peak tetanic force generated by the soleus muscle, when comparing PLA (BF) to PLA (AF) and PG (BF) to PG (AF). Therefore, as a consequence, the twitch/tetanus ratio was significantly reduced after fatigue compared to before fatigue. Despite fatigue ensuing, the contraction time was unaffected by *P. glandulosa* treatment, remaining constant throughout. Ten weeks of *P. glandulosa* treatment sufficiently increased force generated by the soleus muscle, as depicted by the significantly elevated twitch- and peak tetanic force production at baseline (PG (AF) vs. PLA (AF)). *P. glandulosa* treatment also resulted in a significantly increased half-relaxation time post-fatigue, compared to the untreated controls [Table 2].

DISCUSSION

Figure 8:
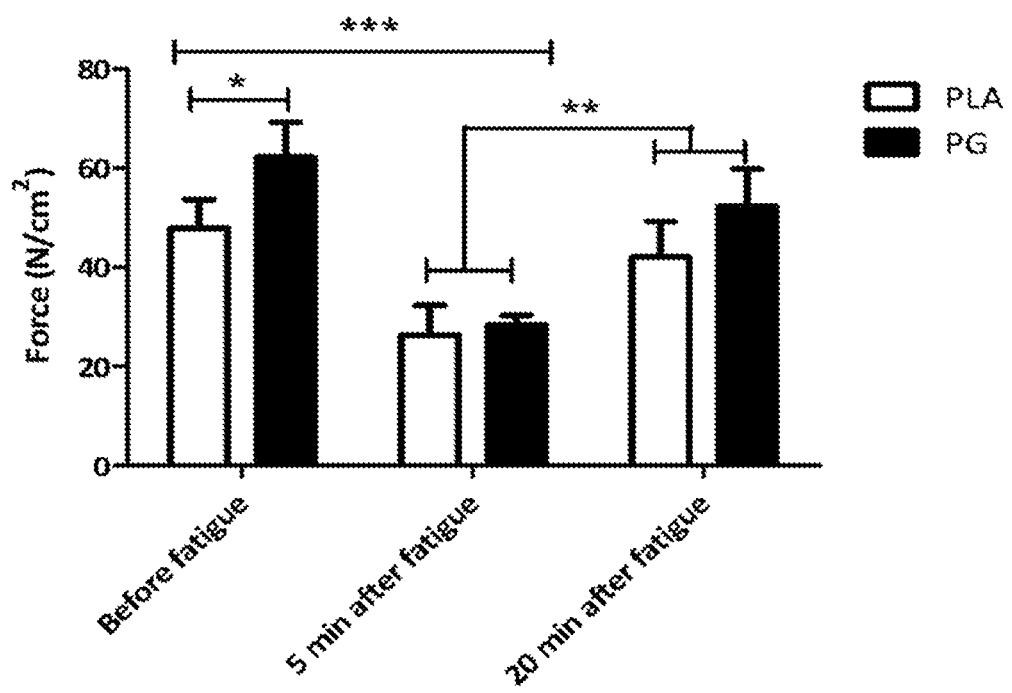
FIG. 8 shows tetanic force production before, 5- and 20 min after fatigue. Tetanic contractions were generated by stimulating the muscle at its supra-maximal voltage at a frequency of 40 Hz. The data are expressed as mean±SEM; Analysis by two-way ANOVA; n=10; * $p<0.05$ PLA vs. PG (Before fatigue); ** $p<0.001$ PLA vs. PLA (5 min vs. 20 min); PG vs. PG (5 min vs. 20 min); *** p<0.0001 PLA vs. PLA (Before fatigue vs. 5 min); PG vs. PG (Before fatigue vs. 5 min).

In this study, the Applicant examined the possible strength-increasing effects of *P. glandulosa* on soleus muscle during electrical field stimulation of healthy rats. The tetanic force generated before fatigue as well as 5 minutes and 20 minutes after fatigue (FIG. 8). From this data it is clear that the force generated 5 minutes after the fatigue protocol was significantly lower than the force generated before fatigue. This is a good indication that the muscles were indeed exhausted, post-fatigue protocol. However, the soleus muscle could regain its force after a 20 minute resting period, as seen in FIG. 8. 20 minutes after fatigue, the force generated is similar to the initial force (before fatigue).

Another aspect which also changes during exercise-induced fatigue is the slowing of muscle relaxation [Allen et al., 2008]. In the present study, there was no significant difference in the initial phase of half-relaxation time in either the control group or the treated group before and after fatigue (Table 2). However, when rats were treated with *P. glandulosa* for 16 weeks and electrically stimulated to fatigue (PG (AF)), their soleus muscles relaxed at a significantly slower rate than the soleus muscles of the untreated rats, 5 minutes after fatigue (PLA (AF)) (Table 2).

Importantly, the soleus muscles of the treated rats (PG) generated significantly higher force when the muscle was stimulated to generate a single twitch or tetanus (Table 2), prior to the induction of fatigue. This same phenomenon was observed during the force-frequency relationship determination. As depicted in FIG. 6(A), the force generated by the soleus muscle of the untreated rats incrementally increased to reach its maximum force at 40 Hz, whereafter the generated force slowly decreased again. Although a similar trend was observed in the treated group, the specific force generated by the soleus muscles of the treated rats was significantly higher at all the different frequencies (FIG. 6(A)). FIG. 6(B), representing the % of maximum force generated at each frequency, shows the similar trend in which both treated and untreated soleus muscles generated force after being stimulated at the respective frequencies. A 20 minute resting period allowed the muscle to recover most of its initial force in both the control (PLA) and treated (PG) groups, when compared to the force generated directly after fatigue (5 minutes). It is known that exercise-induced fatigue is reversible and that after a modest resting period the muscle is able to generate the same force as it did before fatigue set in [Allen et al., 2008]. Therefore, one can assume that the augmented effect on force seen in this study will persist if the muscle is left to completely recover.

The magnitude of muscle force generation is determined mainly by the size of the muscle and the muscle fiber type [Maughan et al., 1983; Lee et al., 2013]. In this study, no significant difference in the biometrics, i.e. the mass, length and width, of the muscles was found in the different experimental groups, and therefore the muscles seemed phenotypically similar (Table 1). A possible explanation for the increase in muscle strength might be that *P. glandulosa* treatment led to the transition of the muscle fiber type, i.e. from a slow-twitch to a fast-twitch phenotype. It is known that not all muscle fibers are the same and that they differ with regards to numerous factors such as metabolism, contraction duration and the time it takes to develop maximum tension. Skeletal muscle fibers are divided into mainly three categories, oxidative slow-twitch fibers, oxidative fast-twitch fibers and glycolytic fast-twitch fibers. According to the results obtained from this study, it seems as if the transition was from an oxidative slow-twitch to an oxidative fast-twitch phenotype. The oxidative slow-twitch fibers and the oxidative fast-twitch fibers react similarly with regards to fatigue development, i.e. they have both been found to be "fatigue-resistant" [Sllverthorn, 2004]. This similarity with regards to fatigue development can also be seen in the data from this study, as there were no significant differences observed between the treated and untreated groups. These muscles fatigued at the same rate. In addition, the time it takes for oxidative fast-twitch fibers to develop maximum tension are faster than that of the oxidative slow-twitch fibers [Sllverthorn, 2004]. This phenomenon is also evident in these results, as the contraction time of the muscles in the untreated group is relatively slower than that of the treated group (Table 2), i.e. the muscles of the treated animals contracted at a faster rate and therefore reached its maximum tension faster. Motor units containing fast-twitch fibers are typically larger than motor units containing slow-twitch fibers. This difference inevitably means that when a single fast-twitch fiber motor unit is stimulated, more muscle fibers contract than when a slow-twitch fiber motor unit is stimulated. Therefore, since more fibers are stimulated to contract in fast-twitch fiber motor units, more force are produced by fast-twitch fibers. Thus muscle composed of a high proportion of slow-twitch fibers will be relatively weaker than a muscle of similar size with a high proportion of fast-twitch fibers.

REFERENCES

1. Quintero, A. J.; Wright, V. J.; Fu, F. H.; Haurd, J. Stem cells for the treatment of skeletal muscle injury. *Clin. Sports Med.* 2009, 28, 1-11.
2. Lovering, R. M. Physical therapy and related interventions. In *Skeletal Muscle Damage and Repair*; Tiidus, P. M., Ed.; Human Kinetics: Champaign, Ill., USA, 2008; pp. 219-230.
3. Smith, C.; Kruger, M. J.; Smith, R. M.; Myburgh, K. H. The inflammatory response to skeletal muscle injury: Illuminating complexities. *J. Sports Med.* 2008, 38, 947-969.
4. Järvinen, T. A.; Järvinen, T. L.; Kääriäinen, M.; Kalimo, H.; Järvinen, M. Muscle injuries: Biology and treatment. *Am. J. Sports Med.* 2005, 33, 745-764.
5. Tidball, J. G. Inflammatory processes in muscle injury and repair. *Am. J. Physiol. Regul. Integr. Comp. Physiol.* 2005, 288, 345-353.
6. Arrington, E. D.; Miller, M. D. Skeletal muscle injuries. *Orthop. Clin. North Am.* 1995, 26, 411-422.
7. Myburgh, K. H.; Kruger, M. J.; Smith, C. Accelerated skeletal muscle recovery after in vivo polyphenol administration. *J. Nutr. Biochem.* 2012, 23, 1072-1079.
8. Summan, M.; Warren, G. L.; Mercer, R. R.; Chapman, R.; Hulderman, T.; van Rooijen, N.; Simeonova, P. P. Macrophages and skeletal muscle regeneration: A clodronate-containing liposome depletion study. *Am. J. Physiol. Regul. Integr. Comp. Physiol.* 2006, 290, 1488-1495.
9. Fielding, R. A.; Manfredi, T. J.; Ding, W.; Fiatarone, M. A.; Evans, W. J.; Cannon, J. G. Acute phase response in exercise. III. Neutrophil and IL-1β accumulation in skeletal muscle. *Am. J. Physiol. Regul. Integr. Comp. Physiol.* 1993, 265, 166-172.
10. Orimo, S.; Hiyamuta, E.; Arahata, K.; Sugita, H. Analysis of inflammatory cells and complement C3 in bupivacaine-induced myonecrosis. *Muscle Nerve* 1991, 14, 515-520.
11. Tidball, J. G.; Villalta, S. A. Regulatory interactions between muscle and the immune system during muscle regeneration. *Am. J. Physiol. Regul. Integr. Comp. Physiol.* 2010, 298, 1173-1187.
12. Hurme, T.; Kalimo, H. Activation of myogenic precursor cells after muscle injury. *Med. Sci. Sports Exerc.* 1992, 24, 197-205.
13. Massimino, M. L.; Rapizzi, E.; Cantini, M.; Libera, L. D.; Mazzoleni, F.; Arslan, P.; Carraro, U. ED2+ macrophages increase selectively myoblast proliferation in muscle cultures. *Biochem. Biophys. Res. Commun.* 1997, 235, 754-759.
14. Shen, W.; Prisk, V.; Foster, W.; Huard, J. Inhibited skeletal muscle healing in cyclooxygenase-2 gene-deficient mice: The role of PGE2 and PGF2alpha. *J. Appl. Physiol.* 2006, 101, 1215-1221.
15. Mishra, D. K.; Friden, J.; Schmitz, M. C.; Lieber, R. L. Anti-inflammatory medication after muscle injury. A treatment resulting in short-term improvement but subsequent loss of muscle function. *J. Bone Joint Surg. Am.* 1995, 77, 1510-1519.
16. Järvinen, M.; Lehto, M. The effect of early mobilization and immobilization on the healing process following muscle injuries. *Sports Med.* 1993, 15, 78-89.
17. Deal, D. N.; Tipton, J.; Rosencrance, E.; Curl, W. W.; Smith, T. L. Ice reduces edema: A study of microvascular permeability in rats. *J. Bone Joint Surg. Am.* 2002, 84, 1573-1578.
18. Hurme, T.; Rantanen, J.; Kalimo, H. Effects of early cryotherapy in experimental skeletal muscle injury. *Scand. J. Med. Sci. Sports* 1993, 3, 46-51.
19. Rantanen, J.; Thorsson, O.; Wollmer, P.; Hurme, T.; Kalimo, H. Effects of therapeutic ultrasound on the regeneration of skeletal muscle myofibers after experimental muscle injury. *Am. J. Sports Med.* 1999, 27, 54-59.
20. Wilkin, L. D.; Merrick, M. A.; Kirby, T. E.; Devor, S. T. Influence of therapeutic ultrasound on skeletal muscle regeneration following blunt contusion. *Int. J. Sports Med.* 2004, 25, 73-77.
21. Best, T. M.; Loitz-Ramage, B.; Corr, D. T.; Vanderby, R. Hyperbaric oxygen in the treatment of acute muscle stretch injuries. Results in an animal model. *Am. J. Sports Med.* 1998, 26, 367-372.
22. Kasemkijwattana, C.; Menetrey, J.; Somogyi, G.; Moreland, M. S.; Fu, F. H.; Buranapanitkit, B.; Watkins, S. S.; Huard, J. Development of approaches to improve the healing following muscle contusion. *Cell Transplant* 1998, 7, 585-598.
23. Plafki, C.; Peters, P.; Almeling, M.; Welslau, W.; Busch, R. Complications and side effects of hyperbaric oxygen therapy. *Aviat. Space Environ. Med.* 2000, 71, 119-124.
24. Kruger, M. J.; Myburgh, K. H.; Smith, C. Contusion injury with chronic in vivo polyphenol supplementation: Leukocyte responses. *Med. Sci. Sport Exerc.* 2014, 46, 225-231.
25. Gibson, S.; Hands, R.; Martinez, C. Medicinal Plants of the Southwest. New Mexico State University (NMSU). 2001. Available online: http://medplant.nmsu.edu/mesquite4.shtm (accessed on 5 Sep. 2014).
26. George, C.; Lochner, A.; Huisamen, B. The efficacy of *Prosopis glandulosa* as antidiabetic treatment in rat models of diabetes and insulin resistance. *J. Ethnopharmacol.* 2011, 137, 298-304.
27. Huisamen, B.; George, C.; Dietrich, D.; Genade, S.; Lochner, A. Cardioprotective and anti-hypertensive effects of *Prosopis glandulosa* in rat model of pre-diabetes. *Cardiovasc. J. Afr.* 2013, 24, 31-37.
28. Stratton, S. A.; Heckmann, R.; Francis, R. S. Therapeutic ultrasound: Its effects on the integrity of a nonpenetrating wound. *J. Orthop. Sports Phys. Ther.* 1984, 5, 278-281
29. Hsu, J. D.; Yao, C. C.; Lee, M. Y.; Kok, L. F.; Wang, P. H.; Tyan, Y. S.; Han, C. P. True cytokeratin 8/18 immunohistochemistry is of no use in distinguishing between primary endocervical and endometrial adenocarcinomas in a tissue microarray study. *Int. J. Gynecol. Pathol.* 2010, 29, 282-289.
30. Lu, D. Y.; Qian, J.; Easley, K. A.; Waldrop, S. M.; Cohen, C. Automated in situ hybridization and immunohistochemistry for cytomegalovirus detection in paraffin-embedded tissue sections. *Appl. Immunohistochem. Mol. Morphol.* 2009, 17, 158-164.
31. Cannon, J. G.; St.; Pierre, B. A. Cytokines in exertion-induced skeletal muscle injury. *Mol. Cell. Biochem.* 1998, 179, 159-167.
32. Kruger, M. J.; Smith, C. Postcontusion polyphenol treatment alters inflammation and muscle regeneration. *Med. Sci. Sports Exerc.* 2012, 44, 872-880.
33. Donnelly, L. E.; Newton, R.; Kennedy, G. E.; Fenwick, P. S.; Leung, R. H.; Ito, K.; Russell, R. E.; Barnes, P. J. Anti-inflammatory effects of resveratrol in lung epithelial cells: Molecular mechanisms. *Am. J. Physiol. Lung Cell. Mol. Physiol.* 2004, 287, 774-783.
34. Andrade, J. M.; Aboy, A. L.; Apel, M. A.; Raseira, M. C.; Pereira, J. F.; Henriques, A. T. Phenolic composition in different genotypes of Guabiju fruit (*Myrcianthes pungens*) and their potential as antioxidant and antichemotactic agent. *J. Food Sci.* 2011, 76, 1181-1187.
35. Fialkow, L.; Wang, Y.; Downey, G. P. Reactive oxygen and nitrogen species as signaling molecules regulating neutrophil function. *Free Radic. Biol. Med.* 2007, 2, 153-164.
36. Lewis, M. S.; Whatley, R. E.; Cain, P.; McIntyre, T. M.; Prescott, S. M.; Zimmerman, G. A. Hydrogen peroxide stimulates the synthesis of platelet-activating factor by endothelium and induces endothelial cell-dependent neutrophil adhesion. *J. Clin. Invest.* 1988, 6, 2045-2055.
37. Judge, A. R.; Dodd, S. L. Oxidative damage to skeletal muscle following an acute bout of contractile claudication. *Atherosclerosis* 2003, 2, 219-224.
38. Mackey, A. L.; Kjaer, M.; Dandanell, S.; Mikkelsen, K. H.; Holm, L.; Dossing, S.; Kadi, F.; Koskinen, S. O.; Jensen, C. H.; Schroder, H. D.; et al. The influence of anti-inflammatory medication on exercise-induced myogenic precursor cell responses in humans. *J. Appl. Physiol.* 2007, 103, 425-431.
39. Mikkelsen, U. R.; Langberg, H.; Helmark, I. C.; Skovgaard, D.; Andersen, L. L.; Kjaer, M.; Mackey, A. L. Local NSAID infusion inhibits satellite cell proliferation in human skeletal muscle after eccentric exercise. *J. Appl. Physiol.* 2009, 107, 1600-1611.
40. Vignaud, A.; Cebrian, J.; Martelly, I.; Caruelle, J. P.; Ferry, A. Effect of anti-inflammatory and antioxidant drugs on the long-term repair of severely injured mouse skeletal muscle. *Exp. Physiol.* 2005, 90, 487-495.
41. Bornemann, A.; Kuschel, R.; Fujisawa-Sehara, A. Analysis for transcript expression of meltrin alpha in normal, regenerating, and denervated rat muscle. *J. Muscle Res. Cell Motil.* 2000, 21, 475-480.
42. Gilpin, B. J.; Loechel, F.; Mattei, M. G.; Engvall, E.; Albrechtsen, R.; Wewer, U. M. A novel, secreted form of human $ADAM_{12}$ (meltrin alpha) provokes myogenesis in vivo. *J. Biol. Chem.* 1998, 273, 157-166.
43. Yagami-Hiromasa, T.; Sato, T.; Kurisaki, T.; Kamijo, K.; Nabeshima, Y.; Fujisawa-Sehara, A. A metalloprotease-disintegrin participating in myoblast fusion. *Nature* 1995, 377, 652-656.
44. Cao, Y.; Zhao, Z.; Gruszczynska-Biegala, J.; Zolkiewska, A. Role of metalloprotease disintegrin $ADAM_{12}$ in determination of quiescent reserve cells during myogenic differentiation in vitro. *Mol. Cell. Biol.* 2003, 23, 6725-6738.
45. Rantanen, J.; Hurme, T.; Lukka, R.; Heino, J.; Kalimo, H. Satellite cell proliferation and the expression of myogenin and desmin in regenerating skeletal muscle: Evidence for two different populations of satellite cells. *Lab. Invest.* 1995, 72, 341-347.
46. Vater, R.; Cullen, M.; Harris, J. The fate of desmin and titin during the degeneration and regeneration of the soleus muscle of the rat. *Acta Neuropathol.* 1992, 84, 278-288.
47. Creuzet, S.; Lescaudron, L.; Li, Z.; Fontaine-Perus, J. MyoD, myogenin, and desmin-nls-lacZ transgene emphasize the distinct patterns of satellite cell activation in growth and regeneration. *Exp. Cell Res.* 1998, 243, 241-253.
48. Przewoźniak, M.; Czaplicka, I.; Czerwińska, A. M.; Markowska-Zagrajek, A.; Moraczewski, J.; Stremiriska, W.; Jańczyk-llach, K.; Ciemerych, M. A.; Brzoska, E. Adhesion proteins—an impact on skeletal myoblast differentiation. *PLoS One* 2013, 8.
49. Vaittinen, S.; Lukka, R.; Sahlgren, C.; Hurme, T.; Rantanen, J.; Lendahl, U.; Eriksson, J. E.; Kalimo, H. The expression of intermediate filament protein nestin as related to vimentin and desmin in regenerating skeletal muscle. *J. Neuropathol. Exp. Neurol.* 2001, 60, 588-597.
50. Allen, D. G., Lamb, G. D., Westerblad, H. 2008. Skeletal muscle fatigue: cellular mechanisms. *Physiological Reviews,* 88: 287-332.
51. Ariano, M. A., Armstrong, R. B., Edgerton, V. R. 1973. Hindlimb muscle fiber populations of five mammals. *Journal of Histochemistry and Cytochemistry,* 21: 51-55.
52. Belluardo, N., Westerblad, H., Mudó, G., Casabona, A., Bruton, J., Caniglia, G., Pastoris, O., Grassi, F., Ibáñez, C. F. 2001. Neuromuscular junction disassembly and muscle fatigue in mice lacking neurotrophin-4. *Molecular and Cellular Neuroscience,* 18: 56-67.
53. Bruton, J., Tavi, P., Aydin, J., Westerblad, H., Lännergren, J. 2003. Mitochondrial and myoplasmic $[Ca^{2+}]$ in single fibres from mouse limb muscles during repeated tetanic contractions. *Journal of Physiology,* 551: 179-190.
54. Bucci, L. R. 2000. Selected herbals and human exercise performance. *American Journal of Clinical Nutrition,* 72: 624S-636S.
55. Calfee, R., Fadale, P. 2006. Popular Ergogenic Drugs and Supplements in Young Athletes. *Pediatrics,* 117: e577-e589.
56. Chen, Y. Z., Lin, F., Li, P. P. 2011. Anti-fatigue effect of Renshen Yangrong decoction in mice *Chinese Journal of Integrative Medicine,* 17: 770-704.
57. Close, G. L., Ashton, T., McArdle, A., Jackson, M. J. 2005. Microdialysis studies of extracellular reactive oxygen species in skeletal muscle: factors influencing the reduction of cytochrome c and hydroxylation of salicylate. *Free Radical Biology and Medicine,* 39: 1460-1467.
58. Demirel, H. A., Powers, S. K., Naito, H., Hughes, M., Coombes, J. S. 1999. Exercise-induced alterations in skeletal muscle myosin heavy chain phenotype: dose-response relationship. *Journal of Applied Physiology,* 86: 1002-1008.
59. El-Khoury, R., Bradford, A., O'Halloran, K. D. 2012. Chronic hypobaric increases isolated rat fast-twitch and slow-twitch limb muscle force and fatigue. *Physiological Research,* 61: 195-201.
60. Fitts, R. H. 1994. Cellular mechanisms of muscle fatigue. *Physiological Reviews,* 74: 49-94.
61. Fitts, R. H., McDonald, K. S., Schluter, J. M. 1991. The determinants of skeletal muscle force and power: their adaptability with changes in activity pattern. *Journal of Biomechanics,* 24: 111-122.
62. George, C., Lochner, A., Huisamen, B. 2011. The efficacy of *Prosopis glandulosa* as antidiabetic treatment in rat models of diabetes and insulin resistance. *Journal of Ethnopharmacology,* 137: 298-304.

63. Gordon, C. S., Serino, A. S., Krause, M. P., Campbell, J. E., Cafarelli, E., Adegoke, O. A., Hawke, T. J., Riddell, M. C. 2010. Impaired growth and force production in skeletal muscles of young partially pancreatectomized rats: a model of adolescent type 1 diabetic myopathy? *PLoS One* 5, e14032.

64. Grivetti, L. E., Applegate, E. A. 1997. From Olympia to Atlanta: a cultural historical perspective on diet and athletic training. *Journal of Nutrition*, 127: 860-868.

65. Harding, G. B. 1987. The status of *Prosopis* spp. as a weed. *Applied Plant Science*, 1: 43-48.

66. Hasegawa, A., Suzuki, S., Matsumoto, Y., Okubo, T. 1997. In vivo fatiguing contraction of rat diaphragm produces hydroxyl radicals. *Free Radical Biology and Medicine*, 22: 349-354.

67. Higashiura, K., Ura, N., Takada, T., Agata, J., Yoshida, H., Miyazaki, Y., Shimamoto, K. 1999. Alteration of muscle fiber composition linking to insulin resistance and hypertension in fructose-fed rats. *American Journal of Hypertension*, 12: 596-602.

68. Huisamen, B., George, C., Dietrich, D., Genade, S., Lochner, A. 2013. Cardioprotective and anti-hypertensive effects of *Prosopis glandulosa* in rat model of pre-diabetes. *Cardiovascular Journal of Africa*, 24: 31-37.

69. Jurriaanse, A. 1973. Are they fodder trees? *Pamphlet 16. Department of Forestry, South Africa*.

70. Lee, S. S., de Boef, Miara, M., Arnold, A. S., Biewener, A. A., Wakeling, M. 2013. Recruitment of faster motor units is associated with greater rates of fascicle strain and rapid changes in muscle force during locomotion. *Journal of Experimental Biology*, 216: 198-207.

71. Lunde, P. K., Sejersted, O. M., Schiøtz Thorud, H. M., Tennessen, T., Henriksen, U. L., Christensen, G., Westerblad, H., Bruton, J. 2006. Effects of congestive heart failure on $Ca^{2+}$ handling in skeletal muscle during fatigue. *Circulation Research*, 98: 1514-1519.

72. Maughan, R. J., Watson, J. S., Weir, J. 1983. Strength and cross-sectional area of human skeletal muscle. *Journal of Physiology*, 338: 37-49.

73. McArdle, F., Pattwell, D. M., Vasilaki, A., McArdle, A., Jackson, M. J. 2005. Intracellular generation of reactive oxygen species by contracting skeletal muscle cells. *Free Radical Biology and Medicine*, 39: 651-657.

74. Pette, D., Staron, R. S. 2001. Transitions of muscle fiber phenotypic profiles. *Histochemistry and Cell Biology*, 115: 359-372.

75. Reid, M. B., Haack, K. E., Franchek, K. M., Valberg, P. A., Kobzik, L., West, M. S. 1992. Reactive oxygen in skeletal muscle. I. Intracellular oxidant kinetics and fatigue in vitro. *Journal of Applied Physiology*, 73: 1797-1804.

76. Roots, H., Ball, G., Talbot-Ponsonby, J., King, M., McBeath, K., Ranatunga, K. W. 2009. Muscle fatigue examined at different temperatures in experiments on intact mammalian (rat) muscle fibers. *Journal of Applied Physiology*, 6: 378-384.

77. Schiaffino, S., Reggiani, C. 2011. Fiber types in mammalian skeletal muscles. *Physiological Reviews*, 91: 1447-531.

78. Schiaffino, S., Sandri, M., Murgia, M. 2007. Activity-dependent signaling pathways controlling muscle diversity and plasticity. *Physiology (Bethesda)*, 22: 269-278.

79. Segal, S. S, Faulkner, J. A, White, T. P. 1986. Skeletal muscle fatigue in vitro is temperature dependent. *Journal of Applied Physiology*, 61:660-665.

80. Silverthorn, D. U. 2004. Skeletal muscle, in W. C. Ober, C. W. Garrison, A. C. Silverthron, B. R. Johnson (eds). *Human Physiology: An integrated approach*. San Francisco: Pearson, Benjamin Cummings. 391-413.

81. Simpson, B. B. 1977. Mesquite: its biology in two desert scrub ecosystems. Hutchinson and Ross, Dowden.

82. Thein, L. A., Thein, J. M., Landry, G. L. 1995. Ergogenic aids. *Physical Therapy*, 75: 426-39.

83. Vasilaki, A., Mansouri, A., Remmen, H., van der Meulen, J. H., Larkin, L., Richardson, A. G., McArdle, A., Faulkner, J. A,; Jackson, M. J. 2006. Free radical generation by skeletal muscle of adult and old mice: effect of contractile activity. *Aging Cell*, 5: 109-117.

84. Wang, J., Li, S., Fan, Y., Chen, Y., Liu, D., Cheng, H., Gao, X., Zhou, Y. 2010. Anti-fatigue activity of the water-soluble polysaccharides isolated from Panax ginseng C. A. Meyer. *Journal of Ethnopharmacology*, 130: 421-423.

85. Wang, L., Higashiura, K., Ura, N., Miura, T., Shimamoto, K. 2003. Chinese medicine, Jiang-Tang-Ke-Li, improves insulin resistance by modulating muscle fiber composition and muscle tumor necrosis factor-alpha in fructose-fed rats. *Hypertension Research*, 26: 527-532.

86. Westerblad, H., Allen, D. G. 1993. The contribution of $[Ca^{2+}]_i$ to the slowing of relaxation in fatigued single fibers from mouse skeletal muscle. *Journal of Physiology*, 468: 729-740.

87. Westerblad, H., Lännergren, J., Allen, D. G. 1997. Slowed relaxation in fatigued skeletal muscle fibers of *Xenopus* and mouse. Contribution of $[Ca^{2+}]_i$ and crossbridges. *Journal of General Physiology*, 109: 385-399.

88. Williams, M. 2006. Dietary Supplements and Sports Performance: Metabolites, Constituents, and Extracts. *Journal of the International Society of Sports Nutrition* 3: 1-5.

89. You, L., Zhao, M., Regenstein, J. M., Ren, J. 2011. In vitro antioxidant activity and in vivo anti-fatigue effect of loach (*Misgurnus anguillicaudatus*) peptides prepared by papain digestion. *Food Chemistry*, 124: 188-194.

90. Yu, F. R., Liu, Y., Cui, Y. Z. Chan, E. Q., Xie, M. R., McGuire, P. P., Yu, F. H. 2010. Effects of a flavonoid extract from *Cynomorium songaricum* on the swimming endurance of rats. *American Journal of Chinese Medicine*, 38: 65-73.

91. Yu, F. R., Lu, S. Q., Yu, F. H., Feng, S. T., McGuire, P. M., Li, R., Wang, R. 2006. Protective effects of polysaccharide from *Euphorbia kansui* (Euphorbiaceae) on the swimming exercise-induced oxidative stress in mice. *Canadian Journal of Physiology and Pharmacology*, 84: 1071-1079.

92. Yuan, Y., Shi, X. E., Liu, Y. G., Yang, G. S. 2011. FoxO1 regulates muscle fiber-type specification and inhibits calcineurin signaling during C2C12 myoblast differentiation. *Molecular and Cellular Biochemistry*, 348: 77-87.

93. Zheng, X., Long, W., Liu, G., Zhang, X., Yang, X., 2012. Effect of seabuckthorn (*Hippophae rhamnoides* ssp. *sinensis*) leaf extract on the swimming endurance and exhaustive exercise-induced oxidative stress of rats. *Journal of the Science of Food and Agriculture*, 92: 736-742.

94. Zimmermann, H. G. 1991. Biological control of mesquite, *Prosopis* spp (Fabaceae), in South Africa. *Agriculture, Ecosystems and Environment*, 37: 175-186.

The invention claimed is:

1. A method of treating a muscle injury in a subject in need thereof comprising administering to said subject an effective amount of a composition consisting essentially of a dried powder of *Prosopis glandulosa* (*P. glandulosa*) pods.

2. A method according to claim 1, wherein the composition is orally administered to the subject.

3. A method according to claim 2, wherein the composition is administered in a formulation which is a tablet, sublingual tablet, wafer, sachet, capsule, suspension, syrup, powder, liquid beverage or edible bar.

4. A method according to claim 1, wherein the composition is topically administered to the subject.

5. A method according to claim 4, wherein the composition is administered in a formulation selected from a suspension, gel, cream or ointment, whereby the composition is applied to the region of the muscle injury.

6. A method according to claim 1, wherein the composition is administered to the subject by way of injection.

7. A method according to claim 1, wherein the muscle injury is skeletal muscle injury.

8. A method according to claim 1, wherein the muscle injury is a direct impact injury.

9. A method according to claim 8, wherein the direct impact injury is a contusion injury.

10. A method according to claim 1, wherein the subject is a human.

11. A method according to claim 1, wherein the composition is administered to the subject at a daily dosage of from about 50 to about 200 mg/kg/day.

12. A method according to claim 1, wherein the composition is administered to the subject at a daily dosage of about 100 mg/kg/day.

13. A method according to claim 1, wherein administration of the composition to the subject reduces or minimizes inflammation caused by the muscle injury.

\* \* \* \* \*